US010663618B2

(12) United States Patent
Summers et al.

(10) Patent No.: US 10,663,618 B2
(45) Date of Patent: May 26, 2020

(54) METHODS TO DETERMINE CONDITIONS OF A HYDROCARBON RESERVOIR

(71) Applicant: ExxonMobil Upstream Research Company, Spring, TX (US)

(72) Inventors: Zarath M. Summers, High Bridge, NJ (US); A. Lucie N'Guessan, Houston, TX (US); Aaron B. Regberg, Houston, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 269 days.

(21) Appl. No.: 15/634,793

(22) Filed: Jun. 27, 2017

(65) Prior Publication Data

US 2018/0003690 A1 Jan. 4, 2018

Related U.S. Application Data

(60) Provisional application No. 62/357,597, filed on Jul. 1, 2016, provisional application No. 62/357,587, filed on Jul. 1, 2016, provisional application No. 62/357,595, filed on Jul. 1, 2016.

(51) Int. Cl.
| | | |
|---|---|---|
| *C12Q 1/68* | (2018.01) | |
| *C07H 21/00* | (2006.01) | |
| *C12Q 1/64* | (2006.01) | |
| *G01V 9/00* | (2006.01) | |
| *G01N 33/28* | (2006.01) | |
| *C12Q 1/6888* | (2018.01) | |
| *C12Q 1/689* | (2018.01) | |
| *G01N 33/24* | (2006.01) | |

(52) U.S. Cl.
CPC ............... *G01V 9/007* (2013.01); *C12Q 1/64* (2013.01); *C12Q 1/689* (2013.01); *C12Q 1/6888* (2013.01); *G01N 33/24* (2013.01); *G01N 33/241* (2013.01); *G01N 33/2823* (2013.01); *C12Q 2600/158* (2013.01)

(58) Field of Classification Search
CPC . C12Q 1/68; C12Q 1/64; C07H 21/00; G01V 9/007; G01N 33/2823
See application file for complete search history.

(56) References Cited

U.S. PATENT DOCUMENTS

| | | | |
|---|---|---|---|
| 4,633,182 A * | 12/1986 | Dzwinel .................. | G01V 3/12 324/335 |
| 6,613,520 B2 | 9/2003 | Ashby | |
| 6,852,495 B2 | 2/2005 | Kojima | |
| 7,297,661 B2 | 11/2007 | Beyer et al. | |
| 7,459,548 B2 | 12/2008 | Brolaski et al. | |
| 7,571,644 B2 | 8/2009 | Ibrahim et al. | |
| 7,762,131 B2 | 7/2010 | Ibrahim et al. | |
| 8,071,285 B1 | 12/2011 | Lawyer et al. | |
| 8,071,295 B2 | 12/2011 | Ashby | |
| 8,120,362 B2 | 2/2012 | Combee | |
| 8,361,725 B2 | 1/2013 | Russell et al. | |
| 8,476,011 B1 | 7/2013 | Short | |
| 8,476,016 B2 | 7/2013 | Ashby | |
| 8,877,918 B2 | 11/2014 | Ozeki et al. | |
| 8,883,417 B2 | 11/2014 | Jacobs et al. | |
| RE45,349 E | 1/2015 | Short | |
| 8,950,251 B2 | 2/2015 | Valentine | |
| 9,145,553 B2 | 9/2015 | Hurt, Jr. et al. | |
| 9,146,225 B2 | 9/2015 | Pottorf et al. | |
| 9,416,356 B2 | 8/2016 | Gundling | |
| 9,528,105 B2 | 12/2016 | Chen et al. | |
| 9,540,636 B2 | 1/2017 | Brahmasandra et al. | |
| 9,593,160 B2 | 3/2017 | Ingber et al. | |
| 9,612,231 B2 | 4/2017 | Pottorf et al. | |
| 2002/0086313 A1 | 7/2002 | Kilbane, II et al. | |
| 2002/0120429 A1 | 8/2002 | Ortoleva | |
| 2003/0211494 A1* | 11/2003 | Hreggvidsson ...... | C12N 9/2417 506/10 |
| 2004/0209249 A1 | 10/2004 | Aevarrson et al. | |
| 2006/0154306 A1* | 7/2006 | Kotlar .................... | G01V 9/007 435/7.2 |

(Continued)

FOREIGN PATENT DOCUMENTS

| | | |
|---|---|---|
| CN | 102154453 | 8/2011 |
| CN | 102732504 A | 10/2012 |
| CN | 103667255 A | 3/2014 |
| CN | 104630204 A | 5/2015 |
| CN | 104630336 | 5/2015 |
| CN | 104651350 | 5/2015 |
| GB | 2478511 A | 9/2011 |
| WO | WO 2002/059351 A2 | 8/2002 |
| WO | WO 2004/090164 A2 | 10/2004 |

(Continued)

OTHER PUBLICATIONS

DiPippo et al., *Kosmotoga olearia* gen. nov., sp. nov., a thermophilic, anaerobic heterotroph isolated from an oil production fluid. International Journal of Systematic and Evolutionary Microbiology, 59: 2991-3000 (Year: 2009).*

(Continued)

*Primary Examiner* — Ethan C Whisenant

(74) *Attorney, Agent, or Firm* — ExxonMobil Upstream Research Company—Law Department

(57) ABSTRACT

A method of identifying in situ conditions of a hydrocarbon reservoir is disclosed. The method comprises, obtaining a sample from an area of interest, such as a sediment sample or water column sample near a hydrocarbon seep; analyzing the sample to detect lipid, protein, and/or nucleic acid signatures that are indicative of the Thermotogales order; identifying the relative abundance of the different genera and/or species of the Thermotogales present in the sample to generate a taxonomy signature of the sample; and then using the taxonomy signature to determine conditions, such as temperature, of the hydrocarbon reservoir.

17 Claims, 4 Drawing Sheets

(56) References Cited

U.S. PATENT DOCUMENTS

| | | | |
|---|---|---|---|
| 2008/0040086 A1 | 2/2008 | Betancourt et al. | |
| 2008/0147326 A1 | 6/2008 | Ellis | |
| 2009/0071239 A1 | 3/2009 | Rojas et al. | |
| 2009/0186778 A1 | 7/2009 | Stepanauskas et al. | |
| 2010/0015612 A1 | 1/2010 | Pelham et al. | |
| 2010/0086180 A1 | 4/2010 | Wallace | |
| 2010/0163230 A1* | 7/2010 | Kotlar | C09K 8/582 166/272.4 |
| 2010/0257004 A1 | 10/2010 | Perlmutter et al. | |
| 2010/0279290 A1 | 11/2010 | Sleat et al. | |
| 2011/0118983 A1 | 5/2011 | Rowan | |
| 2011/0250582 A1 | 10/2011 | Gates et al. | |
| 2011/0308790 A1 | 12/2011 | Strapoc et al. | |
| 2012/0158306 A1 | 6/2012 | Busche et al. | |
| 2012/0165215 A1* | 6/2012 | Andersen | C12Q 1/6837 506/9 |
| 2013/0030712 A1 | 1/2013 | Ashby | |
| 2013/0030714 A1 | 1/2013 | Ashby | |
| 2013/0091925 A1 | 4/2013 | Darrah et al. | |
| 2013/0116126 A1 | 5/2013 | Ashby et al. | |
| 2013/0157275 A1 | 6/2013 | Park et al. | |
| 2014/0011687 A1 | 1/2014 | Ashby | |
| 2014/0011692 A1 | 1/2014 | Ashby | |
| 2014/0051847 A1 | 2/2014 | Hassan et al. | |
| 2014/0162274 A1 | 6/2014 | Kunin et al. | |
| 2014/0182840 A1 | 7/2014 | Sheehy et al. | |
| 2014/0227723 A1 | 8/2014 | Ingber et al. | |
| 2014/0256055 A1* | 9/2014 | Pottorf | G01V 9/007 436/163 |
| 2014/0288853 A1 | 9/2014 | Dreyfus et al. | |
| 2014/0303895 A1 | 10/2014 | Dreyfus et al. | |
| 2014/0315765 A1 | 10/2014 | McDaniel | |
| 2014/0378319 A1 | 12/2014 | Regberg et al. | |
| 2015/0038348 A1 | 2/2015 | Ashby et al. | |
| 2015/0127313 A1 | 5/2015 | Lawson et al. | |
| 2015/0185126 A1 | 7/2015 | Callahan et al. | |
| 2015/0284810 A1 | 10/2015 | Knight et al. | |
| 2015/0284811 A1* | 10/2015 | Knight | E21B 47/1015 506/2 |
| 2015/0291992 A1 | 10/2015 | Al-moniee et al. | |
| 2015/0354000 A1 | 12/2015 | Borodina et al. | |
| 2016/0289544 A1* | 10/2016 | Lee | C09K 8/68 |

FOREIGN PATENT DOCUMENTS

| | | |
|---|---|---|
| WO | WO 2010/109173 | 9/2010 |
| WO | WO 2013/148442 A1 | 10/2013 |
| WO | WO 2015/103615 | 7/2015 |

OTHER PUBLICATIONS

Hania et al., *Defluviitoga tunisiensis* gen. nov., sp. nov., a thermophilic bacterium isolated from a mesothermic and anaerobic whey digester. International Journal of Systematic and Evolutionary Microbiology 62 :1377 (Year: 2012).*
Huber et al., Thermotogales. Prokaryotes 7 :899 (Year: 2006).*
Jayasinghearachichi et al., *Oceanotoga teriensis* gen. nov., sp. nov., a thermophilic bacterium isolated from offshore oil-producing wells. International Journal of Systematic and Evolutionary Microbiology 61 :554 (Year: 2011).*
Jeanthon et al. Hyperthermophilic and Methanogenic Archaea in Oil Fields. Petroleum Microbiology Ed Olliver et al. ASM Press Washington, DC (Year: 2005).*
Nesbo et al., *Mesotoga prima* gen. nov., sp. nov., the first described mesophilic species of the *Thermotogales*. Extremophiles 16 : 387 (Year: 2012).*
Bryant et al. (1989) "Review of Microbial Technology for Improving Oil Recovery", *SPE Reservoir Engineering*, pp. 151-154.
Hohl et al. (2010), "Energy, Environment and Climate Directorate White Paper", DCO Energy, Environment and Climate Workshop, pp. 1-38.
Li et al. (2014) "Microbial Abudance and Community Composition Influence Production Performance in a Low-Temperature Petroleum Reservoir", *Environmental Science and Technology*, vol. 48, pp. 5336-5344.
Lozano—A et al. (2008) "DNA Extraction from Heavy Oil Contaminated Microcosms and RPOB Gene PCR Amplification", *Actual Biol.*, vol. 30, Issue 88, pp. 7-14.
MacDonald et al. (2002) "Transfer of hydrocarbons from natural seeps to the water column and atmosphere", *Geofluids*, vol. 2, pp. 95-107.
Magoon et al. (1994) "The Petroleum System-From Source to Trap", *AAPG Memoir* 60, pp. 3-24.
Mangelsdorf et al. (2011) "Microbial Lipid Markers Within and Adjacent to Challenger Mound in the Belgica Carbonate Mound Province, Porcupine Basin, Offshore Ireland (IODP Expedition 307)", *Marine Geology*, vol. 282, pp. 91-101.
Nocker A., et al. (2007) "Genotypic Microbial Community Profiling: A Critical Technical Review", Microbiology Ecology, pp. 276-289.
Ozgul (2002), "Geochemical Assessment of Gaseous Hydrocarbons: Mixing of Bacterial and Thermogenic Methane in the Deep Subsurface Petroleum System, Gulf of Mexico Continental Slope", Thesis in partial fulfillment of the requirements for the degree of Master of Science at Texas A&M University, pp. 1-167.
Sandrea et al. (2007) "Global Oil Reserves—Recovery Factors Leave Vast Target for EOR Technologies", *Oil & Gas Journal*, pp. 1-8.
Tringe, S.G., et al. (2005) "Comparative Metagenomics of Microbial Communities", Science, vol. 308, pp. 554-557.
Van Hamme et al. (2003) "Recent Advances in Petroleum Microbiology", *Microbiology and Molecular Biology Reviews*, vol. 67, No. 4, pp. 503-549.
Wang et al. (2015) "Nonequilibirum clumped isotope signals in microbial methane", *Science*, vol. 348, Issue 6233, pp. 428-431.
Lazar et al., Distribution of anaerobic methane-oxidizing and sulfate-reducing communities in the G11 Nyegga pockmark, Norwegian Sea, (Jul. 2011). vol. 100, No. 4, pp. 639-653.
Orphan et al., "Culture-Dependent and Culture-Independent Characterization of Microbial Assemblages Associated with High-Temperature Petroleum Reservoirs", *Applied and Environmental Microbiology*, (Feb. 2011), vol. 66, No. 2, pp. 700-711.
Waldron et al., "Salinity Constraints on Subsurface Archaeal Diversity and Methanogenesis in Sedimentary Rock Rich in Organic Matter", *Applied and Environmental Microbiology*, (Jul. 2007), vol. 73, No. 13, pp. 4171-4179.

* cited by examiner

METHODS TO DETERMINE CONDITIONS OF A HYDROCARBON RESERVOIR

CROSS REFERENCE TO RELATED APPLICATIONS

This application claims the benefit of U.S. Provisional Application No. 62/357,587 filed Jul. 1, 2016, U.S. Provisional Application No. 62/357,595 filed Jul. 1, 2016, and U.S. Provisional Application No. 62/357,597 filed Jul. 1, 2016, the entirety of which are incorporated herein by reference.

FIELD OF THE INVENTION

Described herein are methods for determining in situ conditions of a hydrocarbon reservoir. In particular, the methods utilize microbiological data from hydrocarbon seeps to ascertain in situ conditions of a hydrocarbon reservoir, such as the temperature of a hydrocarbon reservoir.

BACKGROUND

The exploration for and discovery of new oil reserves has become increasingly challenging and costly. Untapped reserves tend to be more difficult to identify and evaluate, and are often located subsea, which further increases the complexity and cost of discovering such reserves. Successful, efficient, and cost effective identification and evaluation of hydrocarbon-bearing reservoirs is therefore very desirable.

In marine exploration, seep detection has become an important tool to identify potential hydrocarbon resources in the subsurface. Oil and gas accumulations often leak hydrocarbons including methane, ethane, propane, butane, naphthalene, and benzene. These hydrocarbons may migrate toward the surface (i.e., the seafloor), through a variety of pathways, such as faults or fracture zones. As such, the seeps become surface expressions of subsurface geological phenomena and can be used to give an indication of the subsurface conditions. In some instances, seeps may not be directly above the accumulation from which they originate but rather have further migrated and mixed with the sea water.

Analysis of fluid and sediment samples that are collected from, in, and around hydrocarbon seeps can be used to determine the presence of a mature source rock. However, such analysis cannot confirm or disprove whether the hydrocarbon seep is also connected to a hydrocarbon reservoir. That is, in some instances, while the seep is emanating from a source rock, the source rock may not be connected to a hydrocarbon reservoir. As such, there is a desire to for methods that enable one to determine whether or not a hydrocarbon seep is connected to a hydrocarbon reservoir.

The microbial ecology of a hydrocarbon seep can provide additional information that may be used to characterize the hydrocarbon reservoir from which the seep emanated. That is, it may be possible to use biological information from the hydrocarbon seep for exploration and hydrocarbon characterization purposes. For example, PCT Publication No. WO 2013/119350 describes using the community function and community structure of a sample ecology from a hydrocarbon seep to determine the location of a hydrocarbon reservoir. Additionally, U.S. Patent Application Publication No. 2006/0154306 describes using genotypic analysis of a sample for the presence of thermophilic or extremophilic microorganisms and comparing the biological profile of the sample to those from reference samples to determine the type of oil, quality of oil, gas/oil ratio, depth, or migration route of the sample. Further, U.S. Pat. No. 8,071,295 describes methods for performing surveys of the genetic diversity of a population, creating a database comprising the survey information, and analyzing the information to correlate the presence of nucleic acid markers with desired parameters in a sample, where the surveys are useful in the fields of geochemical exploration, agriculture, bioremediation, environmental analysis, clinical microbiology, forensic science, and medicine.

However, much of the work used to obtain biological information from hydrocarbon systems has relied on culture-based techniques. These techniques are limited because many of the organisms, particularly those living within a hydrocarbon reservoir, are not able to be cultured. While identifying and finding microbes that have originated in the reservoir and have been transported to the surface would be ideal, it is likely that only a limited number of the microbes would possibly survive transport intact. Thus, relying on culture-based techniques may not be feasible or provide a full representation of the subsurface biodiversity.

In addition, past studies have assumed that organisms living in the subsurface are similar to those at the surface. However, recent evidence indicates that the biodiversity in the subsurface is quite complex and many the subsurface species found have not been identified previously. Thus, with increasing genetic divergence from known reference species, the use of "lab-on-a-chip" type tools (e.g., microarrays using oligonucleotide-type probes or polymerase chain reaction (PCR) methods) that require specific binding of probes to identify certain known target biological species becomes less effective. That is, many of the probe-based methods may be restricted to finding organisms that have some genetic similarity to known organisms, and therefore can potentially fail to identify a large portion of the species within a sample.

Application of microbiology-based tracers has also been used to identify whether thermogenic hydrocarbons are present, by examining where hydrocarbon degradation occurs or is associated with known functions such as bacterial sulfate reduction or reactions that alter fluid properties. However, while these methods are useful for identifying diagnostic organisms or probes associated with a particular function, they do not provide information about the in situ conditions, such as the pressure, temperature, or salinity, within the reservoir.

Therefore, it would be desirable to have improved methods of using biological information from the hydrocarbon seep for exploration and hydrocarbon characterization purposes. For example, there is a need for improved methods for determining whether a hydrocarbon seep is connected to a hydrocarbon reservoir and for methods to characterize the hydrocarbon reservoir from which the seep emanated. For example, there is a need for improved methods for determining in situ conditions of a hydrocarbon reservoir, such as determining the temperature of the hydrocarbon reservoir.

Additional background references may include U.S. Patent Application Publication Nos. 2010/279290, 2011/0118983, 2012/0158306, 2013/0157275, 2014/0227723, 2014/0315765, and 2015/0291992; PCT Application Publication Nos. WO 2010/109173, WO 2012/016215, WO 2015/103165, and WO 2015/103332; GB Patent Application Publication No. 2478511 A; Chinese Patent Application Publication Nos. CN 102154453, CN 104630336, and CN 104651350; Lazar et al., "Distribution of anaerobic methane-oxidizing and sulfate-reducing communities in the Gil Nyegga pockmark, Norwegian Sea, Vol. 100, No. 4, pp. 639-653 (July 2011); Orphan et al., "Culture-Dependent and Culture-Independent Characterization of Microbial Assemblages Associated with High-Temperature Petroleum Reservoirs", *Applied and Environmental Microbiology*, Vol. 66, No. 2, pp 700-711 (February 2011); and Waldron et al., "Salinity Constraints on Subsurface Archaeal Diversity and Methanogenesis in Sedimentary Rock Rich in Organic Matter", *Applied and Environmental Microbiology*, Vol. 73, No. 13, pp 4171-4179 (July 2007).

SUMMARY

Described herein are methods for determining conditions, such as the temperature, of a hydrocarbon reservoir. The methods described herein analyze the microbial community found in a hydrocarbon seep to identify whether the hydrocarbon seep is connected to a hydrocarbon reservoir and to determine properties of the hydrocarbon reservoir.

The methods may comprise obtaining one or more samples near a hydrocarbon seep. For example, the sample may be obtained within a radius of 150 meters, or 125 meters, or 100 meters, or 75 meters, or 50 meters, or 25 meters, or 20 meters, or 15 meters, or 10 meters, or 5 meters, or 3 meters, or 1 meter from the center of the location where the seep is emanating from the seafloor. The sample may be a fluid sample from the water column or a sediment sample from the sea floor.

The sample may be processed to extract the nucleic acids from the sample. The extracted nucleic acids may then be amplified and/or sequenced. The amplified/sequenced nucleic acids are then analyzed to identify genetic markers and/or signatures that are indicative of the presence of one or more microorganisms from the order Thermotogales, and in particular the family of Thermotogaceae. The community structure of the Thermotogales within the sample may then be analyzed to identify microorganisms from one or more of the genera *Defluviitoga, Fervidobacterium, Geotoga, Kosmotoga, Marinitoga, Mesotoga, Oceanotoga, Petrotoga, Thermopallium, Thermosipho,* and *Thermotoga.* In particular, the nucleic acid signature may be analyzed to determine the relative abundance of the genera *Thermotoga, Petrotoga,* and *Kosmotoga* within the sample.

The signatures can then be used to identify the signature of the hydrocarbon reservoir. For example, the hydrocarbon reservoir is identified as having a temperature of less than 60° C. when the community structure of the sample indicates that the sample contains 50-100% of microbes from the genera of *Petrotoga, Kosmotoga,* or a mixture thereof. For example, the hydrocarbon reservoir is identified as having a temperature of from 60 to 80° C. when the community structure of the sample indicates that the sample contains 40 to 100% of microbes from the genera of *Thermotoga,* less than 30% of microbes from the genera of *Petrotoga,* and less than 30% of microbes from the genera of *Kosmotoga.* For example, the hydrocarbon reservoir is identified as having a temperature of greater than 80° C. when the community structure of the sample indicates that the sample contains less than 30% of microbes from the genera of *Thermotoga,* less than 30% of microbes from the genera of *Petrotoga,* less than 30% of microbes from the genera of *Kosmotoga,* and from 30-100% of the microbes that are Archaea.

In some embodiments, the method may further comprise calibrating the genetic signature of the sample obtained near the hydrocarbon seep by comparing the signature to a signature of a sample obtained away from the hydrocarbon seep. For example, the method may comprise obtaining a reference sample (such as a water column sample or a sediment sample from the seafloor) at a location that is radially at least 200 meters, or at least 250 meters, or at least 300 meters, or at least 350 meters, or at least 400 meters, or at least 450 meters, or at least 500 meters away from the center of the location where the seep is emanating from the seafloor. The reference sample may then be subjected to the nucleic acid, lipid, and protein extraction and sequencing to determine the signature of the reference sample. The signature from the hydrocarbon seep sample may then be calibrated by comparing it to the signature from the reference sample.

DETAILED DESCRIPTION OF THE DISCLOSURE

Figure 1:
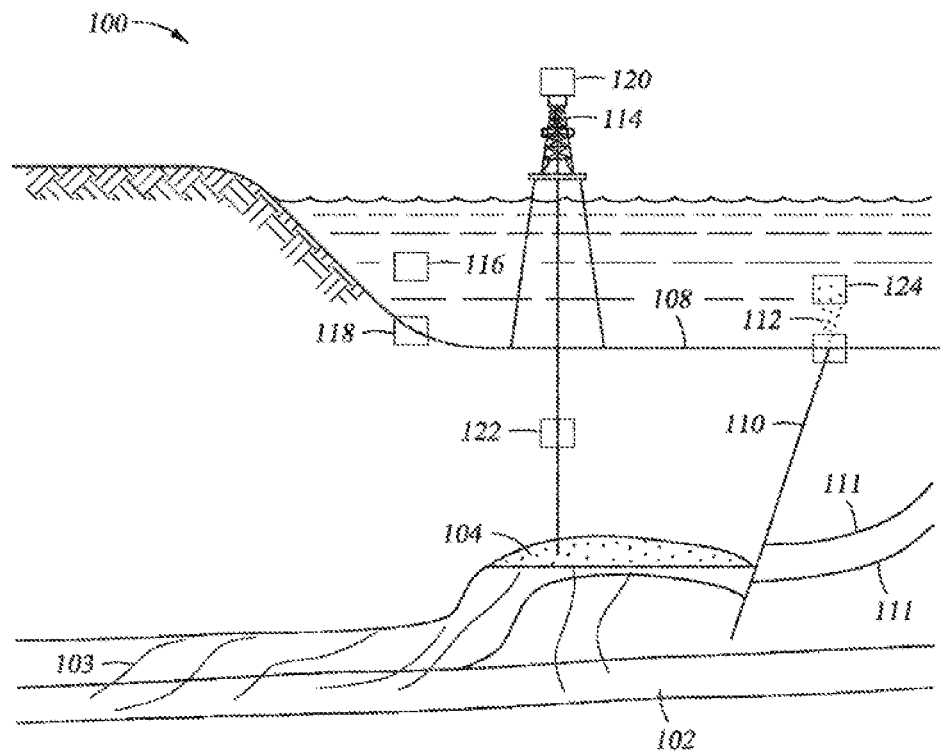
FIG. 1 is a schematic illustrating a cross section view of a hydrocarbon system and an associated seafloor seep.

To the extent the following description is specific to a particular embodiment or a particular use, this is intended to be illustrative only and is not to be construed as limiting the scope of the invention. On the contrary, it is intended to cover all alternatives, modifications, and equivalents that may be included within the spirit and scope of the invention.

Example methods described herein may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement various embodiments of an example methodology. Blocks may be combined or separated into multiple components. Furthermore, additional and/or alternative methodologies can employ additional blocks not shown herein. While the figures illustrate various actions occurring serially, it is to be appreciated that various actions could occur in series, substantially in parallel, and/or at substantially different points in time.

Various terms as used herein are defined below. To the extent a term used in a claim is not defined below, it should be given the broadest possible definition persons in the pertinent art have given that term as reflected in at least one printed publication or issued patent.

"Amplification" is the generation of multiple copies of nucleic acid segments to enhance the analysis of very low amounts of nucleic acids. For example, amplification may be performed by a polymerase chain reaction ("PCR"), which uses a thermostable polymerase enzyme, such as the TAQ enzyme for DNA, to exponentially produce thousands or millions of copies of a DNA segment during a number of thermal cycles. During each cycle, the DNA segments produced in a previous cycle become templates for new copies of that segment. RNA analysis may be performed by reverse transcribing the RNA to create cDNA segments, which may then be amplified.

As used herein, "behavior" encompasses responses to stimuli. For example, the behavior of an organism may indicate the organism's motility, attachment (including biofilm formation), bioluminescence, mineral precipitation, spore formation, etc.

As used herein, "community composition" refers to the composition of the organisms in the system. That is, the community composition is an indication of the types or organisms (e.g., bacteria vs. archaea, or species x vs. species y) that live or exist in the system.

As used herein, "community structure" refers to the abundance of each type of organism in the system. In particular, the community structure is an indication of the relative abundance of the different types of organisms in the system. For example, the community structure may indicate that the system comprises 10% bacteria and 90% archaea. In some embodiments, the community structure may look at only a subset of the organisms within the system and provide an indication of the relative abundance of certain species within the system as compared to other species within the system. For example, the community structure may indicate that the system comprises 25% species x, 40% species y, 30% species z, and 5% of unclassified species.

As used herein, "community function" refers to an indication of the types of metabolic processes the organisms within the system perform. For example, the community function may indicate that the organisms within the system are capable of hydrocarbon degradation, sulfate reduction, iron reduction, fermentation, etc.

As used herein, "DNA analysis" refers to any technique used to amplify and/or sequence DNA contained within the sample. DNA amplification can be accomplished using PCR techniques or pyrosequencing. DNA analysis may also comprise non-targeted, non-PCR based DNA sequencing (e.g., metagenomics) techniques. As a non-limiting example, DNA analysis may include sequencing the hyper-variable region of the 16S rDNA (ribosomal DNA) and using the sequencing for species identification via DNA.

As used herein, "ecology" refers to the study of the interactions between the living and non-living components of a system. In particular, the ecology of a sample includes information about the biology, microbiology, and molecular biology of components of the sample. Of particular reference herein, the ecology of a sample refers to a description of the organisms that live or exist within a sample, and may include parameters such as community composition, community structure, and community function of the organisms within the sample.

As used herein, "ex situ analysis" refers to the analysis of samples outside of their original environment. Culture- or cell-based techniques require that live organisms be captured in order to further study them to make the appropriate assessments are considered ex situ analysis.

The term "field sample" refers to a sample containing material from the natural environment. Field samples include, but are not limited to, samples taken from any soil (encompassing all soil types and depths), water or liquid (encompassing freshwater aquatic or marine habitats), sediment (encompassing marine sediment, lake or river sediment, or mud sediment), or atmospheric dust or particulates. The field sample may include a multitude of species of microorganisms or a single species of microorganism. In preferred embodiments, the samples are field samples taken from the sediment or water column near a hydrocarbon seep. In such a context, the term "near" means the sample is obtained within a radius of 150 meters, or 125 meters, or 100 meters, or 75 meters, or 50 meters, or 25 meters, or 20 meters, or 15 meters, or 10 meters, or 5 meters, or 3 meters, or 1 meter from the center of the location where the seep is emanating from the surface. Reference samples may also be field samples taken from the sediment or water column away from the hydrocarbon seep. In such a context, the term "away" means the reference sample is obtained at least 200 meters, or at least 250 meters, or at least 300 meters, or at least 350 meters, or at least 400 meters, or at least 450 meters, or at least 500 meters away from the center of the location where the seep is emanating from the surface, and in some embodiments, less than 2000 meters, or less than 1750 meters, or less than 1500 meters, or less than 1250 meters, or less than 1000 meters away from the location where the seep is emanating from the surface.

A "geologic model" is a computer-based representation of a subsurface earth volume, such as a petroleum reservoir or a depositional basin. Geologic models may take on many different forms. Depending on the context, descriptive or static geologic models built for petroleum applications can be in the form of a 2-D or 3-D array of cells, to which geologic and/or geophysical properties such as lithology, porosity, acoustic impedance, permeability, or water saturation are assigned (such properties are referred to collectively herein as "reservoir properties"). Many geologic models are constrained by stratigraphic or structural surfaces (for example, flooding surfaces, sequence interfaces, fluid contacts, and/or faults) and boundaries (for example, facies changes). These surfaces and boundaries define regions within the model that possibly have different reservoir properties.

As used herein, "genomics" refers to the study of genomes of organisms, which includes the determination of the entire DNA or RNA sequence of organisms as well as genetic mapping.

A "hydrocarbon" is an organic compound that primarily includes the elements hydrogen and carbon, although nitrogen, sulfur, oxygen, metals, or any number of other elements may also be present in small amounts. As used herein, hydrocarbons generally refer to organic materials (e.g., natural gas and liquid petroleum) that are harvested from hydrocarbon containing sub-surface rock layers, termed reservoirs.

As used herein, "hydrocarbon management" or "managing hydrocarbons" includes hydrocarbon exploration, hydrocarbon extraction, hydrocarbon production, identifying potential hydrocarbon resources, identifying well locations, determining well injection and/or extraction rates, identifying reservoir connectivity, acquiring, disposing of and/or abandoning hydrocarbon resources, reviewing prior hydrocarbon management decisions, and any other hydrocarbon-related acts or activities.

As used herein, "hydrocarbon exploration" refers to any activity associated with determining the location of hydrocarbons in subsurface regions. Hydrocarbon exploration normally refers to any activity conducted to obtain measurements through acquisition of measured data associated with the subsurface formation and the associated modeling of the data to identify potential locations of hydrocarbon accumulations. Accordingly, hydrocarbon exploration includes acquiring measurement data, modeling of the measurement data to form subsurface models, and determining the likely locations for hydrocarbon reservoirs within the subsurface. The measurement data may include seismic data, gravity data, magnetic data, electromagnetic data, and the like.

As used herein, "hydrocarbon development" refers to any activity associated with planning of extraction and/or access to hydrocarbons in subsurface regions. Hydrocarbon development normally refers to any activity conducted to plan for access to and/or for production of hydrocarbons from the subsurface formation and the associated modeling of the data to identify preferred development approaches and methods. By way of example, hydrocarbon development may include modeling of the subsurface formation and extraction planning for periods of production, determining and planning equipment to be utilized and techniques to be utilized in extracting the hydrocarbons from the subsurface formation, and the like.

As used herein, "hydrocarbon production" refers to any activity associated with extracting hydrocarbons from subsurface location, such as a well or other opening. Hydrocarbon production normally refers to any activity conducted to form the wellbore along with any activity in or on the well after the well is completed. Accordingly, hydrocarbon production or extraction includes not only primary hydrocarbon extraction, but also secondary and tertiary production techniques, such as the injection of gas or liquid for increasing drive pressure, mobilizing the hydrocarbon, or treating the well by, for example, chemicals, or hydraulic fracturing the wellbore to promote increased flow, well servicing, well logging, and other well and wellbore treatments.

As used herein, "in situ analysis" refers to the analysis of samples within the environment of interest. This approach is similar to other geochemical measurements, such as pH, temperature, pressure, concentration of dissolved ions, etc., which can be measured using a variety of in situ tools and probes.

As used herein, "lipids" refers to hydrophobic or amphiphilic compounds that compose cell membranes of organisms, energy storage, and signaling molecules.

As used herein, "lipid analysis" refers to quantification and/or description of the phospho-lipids present in a sample. Phospho-lipids are compounds containing two chains of hydrophobic compounds linked together by a hydrophilic head group. Different species of bacteria and archaea produce different types of lipids. Additionally, all known bacterial lipids are joined together with an ester bond while all known archaeal lipids are joined together with an ether bond. Thus, intact lipids can provide information about the community structure or organisms in a sample. Further, as lipid production may vary as a function of temperature, pressure, and/or salinity, lipid analysis may provide information about reservoir conditions. While the hydrophilic head group in a lipid is easily degradable, the remaining hydrophobic chains are quite stable. As such, derivatives of these chains can be used as biomarkers in organic geochemistry to fingerprint oils. Unaltered lipids can be used in a similar matter. Altered lipids can also be used to fingerprint oils in organic geochemistry. Non-intact lipids can provide information about community structure in the past. That is, non-intact lipids can provide information about prior community structures that can be used to indicate that conditions in the community were different at some point of time in the past. Thus, non-intact lipids can allow one to identify areas of past microbiological activity where DNA based markers have already been destroyed.

As used herein, "metabolites" refer to compounds produced by bacteria and/or archaea during respiration or fermentation. For example, acetic acid is an example of a metabolite. Metabolites can provide information about the type of hydrocarbon being used as a substrate as well as information about physical and chemical conditions in the reservoirs. For example, the presence of specific metabolites may indicate or infer the presence of hydrocarbons and/or conditions at depth.

A "microbe" is any microorganism that is of the domain Bacteria, Eukarya, or Archaea. Microbes include bacteria, fungi, nematodes, protozoans, archaebacteria, algae, dinoflagellates, molds, bacteriophages, mycoplasma, viruses, and viroids.

As used herein, a "microarray" is a multiplex lab-on-a-chip that allows many tests to be performed simultaneously or in sequence. It is an array of hundreds to thousands of spots containing probes (or tags) of various types. Lab-on-a-chip and microfluidics devices allow for the analysis of samples using miniaturized laboratory processes, which require small sample sizes, such as less than $10^{-6}$ L of the sample, or less than $10^{-9}$ L of the sample.

The term "nucleic acid" refers to biopolymers used in cells for the transfer of information. Nucleic acids include deoxyribonucleic acid ("DNA"), which is generally found in a nucleus of a eukaryotic cell, and ribonucleic acid ("RNA"), which is generally found in the cytoplasm of a eukaryotic cell. A prokaryotic cell, such as a bacterial or archea cell, does not have a nucleus, and both DNA and RNA may be found in the cytoplasm of the cell. DNA often provides the genetic code for a cell, although a few types of organisms use RNA to carry heritable characteristics. RNA is often associated with the synthesis of proteins from genes on the DNA.

As used herein, "products" refer to proteins, lipids, exopolymeric substances, and other cellular components that organisms produce under a given set of conditions.

As used herein, "proteomics" refers to the description of proteins produced by bacteria and/or archaea. Proteins can be used to describe the function of the most active members of a microbial community. Proteomics can be used to describe community structure, but only if the links between individual species and expressed proteins are clearly understood. Proteins can be separated using two dimensional electrophoresis. The proteins can then be analyzed using a TOF (time of flight) mass spectrometer coupled to a liquid chromatograph or a MALDI (matrix assisted laser desorption/ionization) unit. Since proteins are not easily amplified proteomic analysis in natural samples often requires a large amount of biomass to be successful.

As used herein, "RNA analysis" refers to any technique used to amplify and/or sequence RNA contained within the samples. The same techniques used to analyze DNA can be used to amplify and sequence RNA. RNA, which is less stable than DNA is the translation of DNA in response to a stimuli. Therefore, RNA analysis may provide a more accurate picture of the metabolically active members of the community and may be used to provide information about the community function of organisms in a sample.

A "reservoir" is a subsurface rock formation from which a production fluid can be produced. The rock formation may include granite, silica, carbonates, clays, and organic matter, such as oil, gas, or coal, among others. Reservoirs can vary in size from less than one cubic foot (0.3048 $m^3$) to hundreds of cubic feet (hundreds of cubic meters). The permeability of the reservoir rock may provide paths for production and for hydrocarbons to escape from the reservoir and move to the surface.

A "seep" or "hydrocarbon seep" or "petroleum seep" is a place where hydrocarbons escape to the surface, normally under low pressure or flow. Seeps may occur above either terrestrial or offshore petroleum reservoirs, but may also occur above subsurface deposits of organic material, for example, as the organic material degrades. The hydrocarbons may escape from the reservoir or deposit along geological layers, or through fractures and fissures in the rock.

As used herein, a "sensor" is a device that detects and measures one or more physical, chemical, or biological signals.

As used herein, "sequencing" refers to the determination of the exact order of nucleotide bases in a strand of DNA (deoxyribonucleic acid) or RNA (ribonucleic acid) or the exact order of amino acids residues or peptides in a protein. For example, nucleic acid sequencing can be done using Sanger sequencing or next-generation high-throughput sequencing including but not limited to massively parallel pyrosequencing, Illumina sequencing, or SOLiD sequencing, ion semiconductor sequencing. For example, amino acid sequencing may be done by mass spectrometry and Edman degradation.

"Substantial" when used in reference to a quantity or amount of a material, or a specific characteristic thereof, refers to an amount that is sufficient to provide an effect that the material or characteristic was intended to provide. The exact degree of deviation allowable may in some cases depend on the specific context.

As used herein, "transcriptomics" refers to the amplification and/or sequencing of mRNA (messenger RNA), rRNA (ribosomal RNA), and tRNA (transfer RNA). These types of RNA are used to build and synthesize proteins. Understanding what transcripts are being used allows one to understand what proteins are being produced, and thus provides information about the community function of organisms in a sample.

As used herein, "paleo-seep" refers to an area that is no longer seeping.

Fluids and sediments collected in and around hydrocarbon seeps can be used to describe the presence of a mature source rock. Further, as described herein, the presence or absence, and relative abundance of unique microbial species within the sample can provide an indication of the in situ conditions of the hydrocarbon reservoir from which the seep emanated. That is, by analyzing the microbial signature of the sample from a hydrocarbon seep, one can infer that certain conditions exist in the subsurface reservoir. In particular, the presence of microbes the can survive at extreme conditions can be used as a tracer to identify hydrocarbon seeps connected to reservoirs. Further, information about the community structure and community function of the samples can be used to describe the physical conditions (e.g., temperature and pressure) and chemical conditions (e.g., salinity) of the connected hydrocarbon reservoir.

FIG. 1 illustrates a hydrocarbon system 100 that includes an organic carbon bearing source rock 102 that generates and excretes liquid and gaseous hydrocarbons, which migrate through various migration pathways 103 into a reservoir 104. The hydrocarbons are trapped in the reservoir 104. A sealing interval above the reservoir prevents further hydrocarbon migration out of the reservoir. However, hydrocarbons can escape from the reservoir and migrate toward the surface (shown in FIG. 1 as a seafloor 108) through a variety of pathways, such as faults 110 or fracture zones 111. This hydrocarbon migration can then result in seeps 112 discharging hydrocarbons from the seafloor into the water column. Water samples 124 can be taken at or near a suspected seep 112 to determine the ecology of the associated water column. For example, the sample may be taken within a radius of 150 meters, or 125 meters, or 100 meters, or 75 meters, or 50 meters, or 25 meters, or 120 meters, or 15 meters, or 10 meters, or 5 meters, or 3 meters, or 1 meter, from the center of the location where the seep is emanating from the seafloor 108. A suspected seep may be identified a variety of methods, for example the presence of physical disturbance of the sediment, bubble trains, microbial mats, and oil slicks or sheens at the sea-air interface, may all indicate the presence of an active seep. To control for microorganisms present in the water that are not associated with a seep, a water sample 116 may also be taken in a region where there are no known seeps. Thus, by comparing the microbial signatures of the sample from the seep 124 and the control sample 116 one can determine which organisms have migrated from the subsurface reservoir. Other samples 118 may also be collected from shallow sediment on the seafloor to determine the ecology of the seafloor 108. Once a likely site for the hydrocarbon accumulation has been established, an exploration well 114 can be drilled and one or more core samples 122 can be taken. Likewise, liquid samples may be collected from a production platform 120. Information from the core samples or liquid samples from the production platform can be used to verify or calibrate information determined about the subsurface conditions by the methods described herein.

Figure 2A:
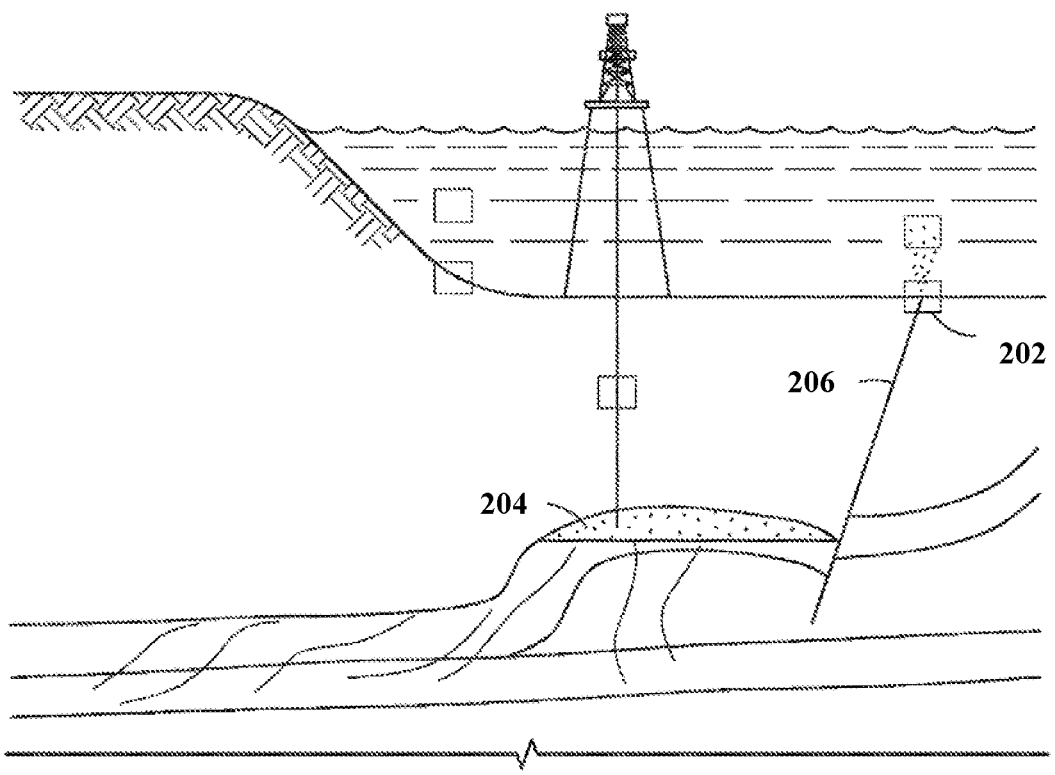
FIGS. 2A, 2B, 2C, and 2D are schematics illustrating cross section views of different types of seafloor hydrocarbon seeps.
Figure 2B:
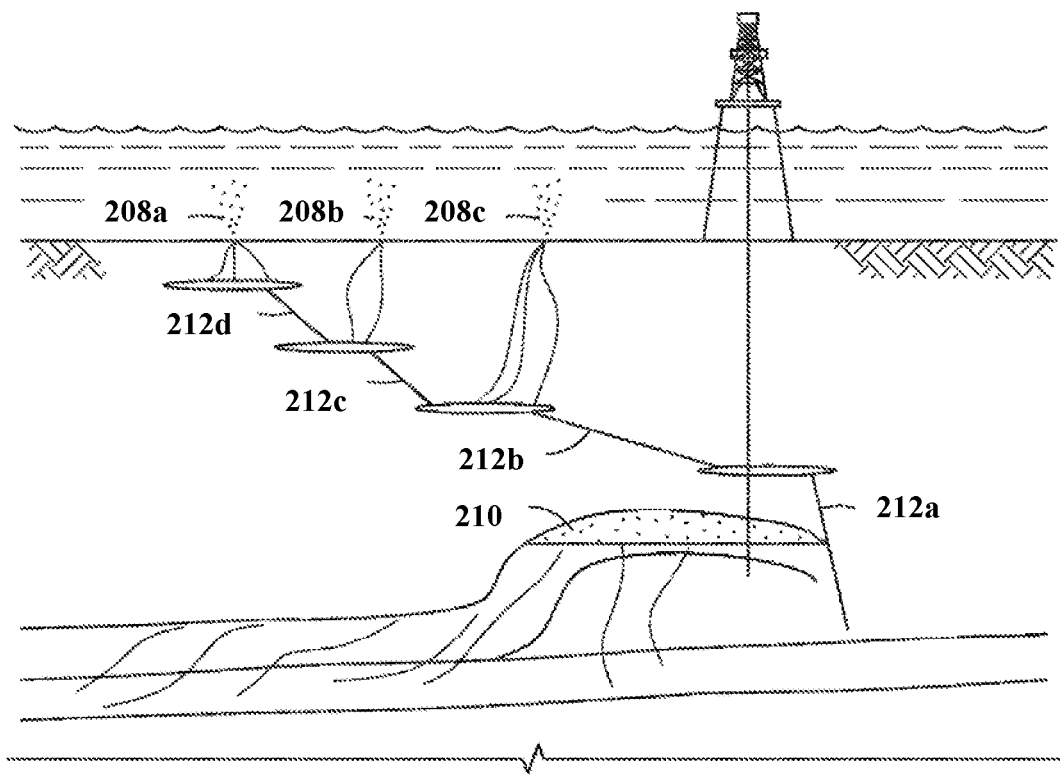
Figure 2C:
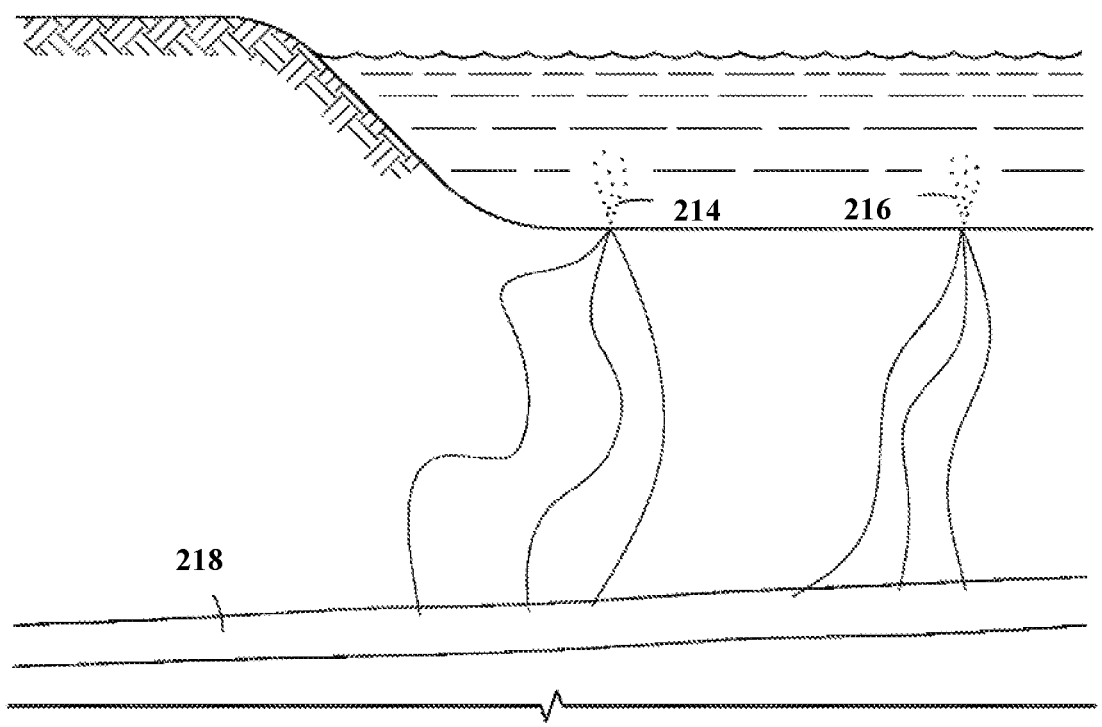
Figure 2D:
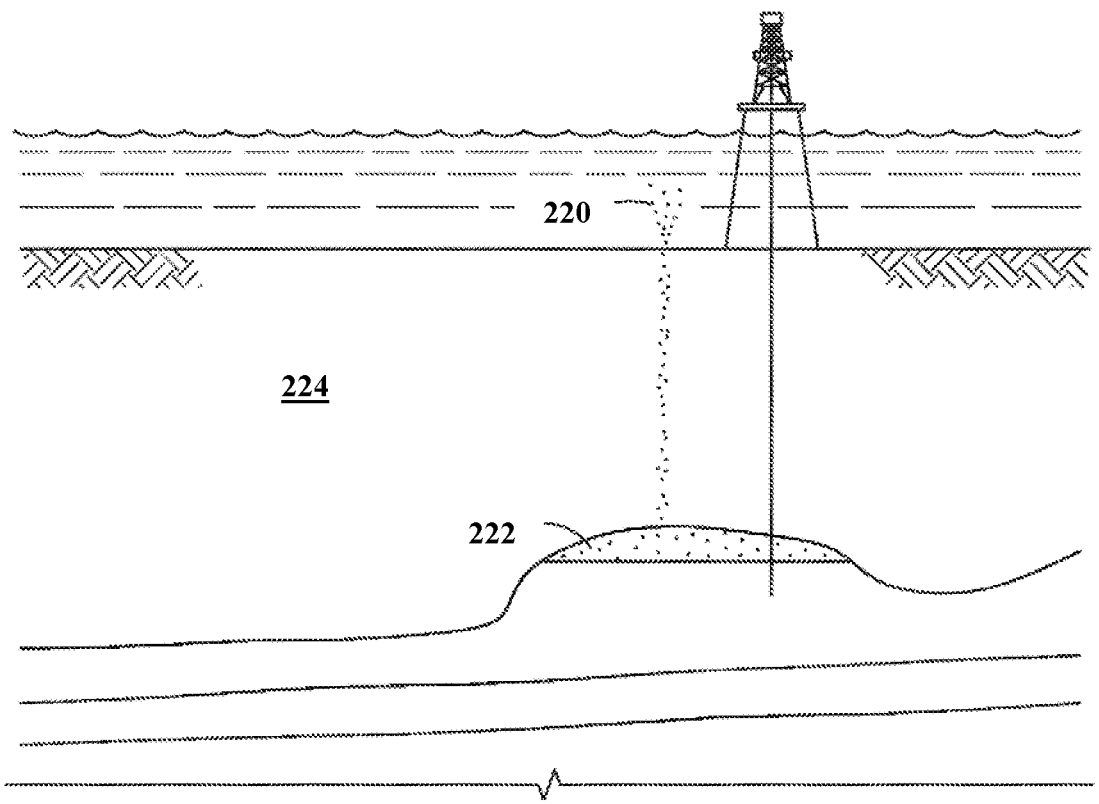

FIGS. 2A to 2D illustrate different types of seafloor hydrocarbon seeps. FIG. 2A is similar to FIG. 1, and shows a seep 202 directly connected to a hydrocarbon reservoir 204 through a fault 206. FIG. 2B shows a series of seeps 208a, 208b, 208c that are indirectly connected to an hydrocarbon reservoir 210 through a series of faults 212a, 212b, 212c, 212d. FIG. 2C shows a pair of seeps 214, 216, independent of any faults that are linked to an actively generating source rock 218 in which there is no reservoir. FIG. 2D shows a fault-independent seep 220 associated with a hydrocarbon reservoir 222. In FIG. 2D, the hydrocarbons in the reservoir 222 overcome the capillary entry pressure of the overlying rock 224 and escape to the surface. As seen in FIGS. 2A to 2D, hydrocarbon seeps can have vastly different physical conditions, such as being connected to a hydrocarbon reservoir in FIGS. 2A, 2B, and 2D versus being independent of a reservoir as seen in FIG. 2C. Further, the hydrocarbon seep can directly emanating from the reservoir as in FIG. 2D, emanate from a fault connected to the reservoir as in FIG. 2A, or emanate from faults that are indirectly connected to a reservoir as in FIG. 2B. The methods and techniques described herein can be used to analyze the microbial signatures of samples taken from the hydrocarbon seep to identify physical and chemical conditions unique to each system, and thus give an indication of what kind of source the hydrocarbons in the seep have emanated from.

Physical and chemical conditions in hydrocarbon reservoirs are typically very different from conditions at the seafloor. Pressure and temperature are both generally higher in hydrocarbon reservoirs than at the seafloor. Additionally, salinity is often higher in hydrocarbon reservoirs than at the seafloor and organic carbon is more abundant in a hydrocarbon reservoir. These differences create different environments for different types of microorganism to thrive in where they otherwise would not. For example, thermophilic and halophilic bacteria have been identified and isolated from hydrocarbon reservoirs that would not normally exist at the seafloor. As these microorganisms are transported to the surface via a hydrocarbon seep they can be detected in samples from the hydrocarbon seep. Furthermore, organisms living at reservoir conditions and/or those that are transported to the seafloor express different proteins and lipids, thereby permitting a determination of reservoir pressure and temperature based on these variables. In the absence of an active hydrocarbon system, the links between the water column, seafloor sediment and subsurface ecology become less clear.

Furthermore, the relative contribution of reservoir ecology to the water column, seafloor sediment, and subsurface rock ecology can be linked to hydrocarbon migration pathways and therefore hydrocarbon system type can be inferred. Samples at seeps that are fed by hydrocarbon reservoirs will share some characteristics with samples taken directly from those reservoirs. The techniques described herein can be combined with physical and chemical measurements to create a complete, coherent description of the ecology of a given sample, and thus with the hydrocarbon reservoir. That is, samples from hydrocarbon seeps that are physically connected to a hydrocarbon reservoir will share ecological characteristics. For example, a sediment sample from a seep will share ecological characteristics with the reservoir where the seeping fluids originated. According to methodologies and techniques described herein, a method is provided explaining how to describe the ecology of a sample and how to relate the ecology of physically disparate samples to physiochemical conditions associated with sample, and thus with the hydrocarbon reservoir.

For example, detailed descriptions of sample ecology will highlight differences in indicator species, and differences in transcripts, lipids, proteins and metabolites can distinguish seeps connected to larger hydrocarbon reservoirs from seeps in which no reservoirs are present.

Organisms contained in samples are characterized for various phenotypes and physiological aspects. For example, the organisms can be cultured and tested for their ability to survive and grow under a variety of environmental conditions such as pressure, temperature, salinity, etc. The ability of organisms to degrade hydrocarbons of interest may also be determined. Organisms exhibiting target characteristics are also isolated and characterized at depth. Molecular characterization typically requires the extraction of components from samples. These components include nucleic acids (e.g., DNA and RNA), proteins, lipids, exopolymeric substances, etc. Analysis of these components requires various techniques which include nucleic acid sequencing, protein sequencing, and/or some sort of separation and/or hybridization.

The methods and techniques described herein can be used to identify members of the order Thermotogale that are unique to hydrocarbon reservoirs with in situ temperatures that range from 40 to 98° C. These hydrocarbon reservoirs may also be characterized with pressures as high as 65 MPa and total dissolved solids concentrations as high as 24%. Thermotogale are known thermophiles and hyperthermopiles, and as described herein it has been found that individual genera and species of the Thermotogale order have distinct optimal growth temperatures. Thus, the community structure of the Thermotogale present in a sample (i.e., the relative abundance of different genera and species of the Thermotogale present in a sample) can be used to identify the temperature of the hydrocarbon reservoir. In particular, the detection of the different genera of Thermotogale can be achieved through nucleic acid sequencing from mixed community DNA using Tehrmotogale specific DNA probes for flouuresence tagging or DNA primers for PCR. Detection of unique proteins using antibodies specific to LPS or proteins of the Thermotogales, or detection of unique membrane lipids, such as diabolic acids, or other lipid derivatives found only in the Thermotogales using various chromatographic methods such as HPLC or LC/MS can be used. As such, the relative abundance of the various Thermotogales present in the sample can be used as indicators of not only the presence of a reservoir, but also the physical condition (e.g., temperature) of the reservoir.

For example, for the different genera of the Thermotogaceae family, if the community structure of the sample indicates that 50-100% of the family is represented by either *Petrotoga* or *Kosmotoga*, or a mixture thereof, and less than 30% is represented by a concentration of the genus *Thermotoga*, this indicates that the reservoir has a temperature of less than 60° C. However, if 40 to 100% of the sample is represented by *Thermotoga*, with both *Petrotoga* and *Kosmotoga* being represented by less than 30% each, this indicates that the hydrocarbon reservoir has a temperature of from 60 to 80° C. Ultra high temperature reservoirs, e.g., those with a temperature of greater than 80° C., are represented by community structures where *Thermotoga* represent less than 30% of the community, *Kosmotoga* represent less than 30% of the community, *Perotoga* represent less than 30% of the community, and from 30-100% of the community include thermophilic and hyperthermophilic Archaea.

According to aspects of disclosed methodologies, a method is provided for using the ecology of a sample from a hydrocarbon seep to determine characteristics of the subsurface hydrocarbon system. An illustrated method is provided with reference to FIG. 3. At block 302 a sample is collected from the sediment near a hydrocarbon seep or the water column associated with a hydrocarbon seep. The samples may be collected by hand or by using a remotely operated vehicle. Sediment samples may come from small sediments coops, push cores, box cores, gravity cores, piston cores, or jumbo piston cores. Liquid samples from the water column may include water and hydrocarbon independently or in a mixture. The sample may be taken within a radius of 150 meters, or 125 meters, or 100 meters, or 75 meters, or 50 meters, or 25 meters, or 20 meters, or 15 meters, or 10 meters, or 5 meters, or 3 meters, or 1 meter, from the center of the location where the seep is emanating from the seafloor.

If the samples are not being analyzed immediately, the samples may be frozen as soon as possible after collection to preserve the integrity of the sample ecology. That is, the sediment, water, and rock/or samples may be frozen as soon after collection as possible to prevent organismal changes within the samples due to the sample being maintained at a different conditions than those at which the sample were collected. For example, the samples may be maintained at a low temperature, such as less than –60° C., or less than –70° C., or less than –80° C., until analyses are performed. In some embodiments, the sample may be maintained at a temperature in the range of –60° C. to –100° C., or from –60° C. to –80° C., until analyses are performed. For samples that are being analyzed in situ, freezing of the samples may not be required.

Once the samples are collected at block 302, the samples are analyzed using various methods to ascertain aspects of the ecology of the sample. For example, the samples may undergo DNA analysis, RNA analysis, metagenomics (including pyrosequencing), proteomics, transcriptomics, lipid analysis, phenotyping, metabolite analysis, organic geochemistry, and inorganic geochemistry analysis. Thus, at block 304 biological material is extracted from the sample. For example, nucleic acids (e.g., DNA and RNA), proteins, and lipids are extracted from the sample. Lipids and proteins can be extracted from the sample and purified using known techniques. For example, the lipids and proteins can be separated from the sample using two dimensional electrophoresis or standard precipitation techniques. The nucleic acids can be extracted from the sample using known techniques. For example, nucleic acids can be extracted from a sediment sample using a sediment DNA extraction technique, such as the MoBio Power Soil DNA extraction kit, or utilizing the method described in U.S. patent application Ser. No. 15/600,161, the disclosure of which is incorporated herein by reference.

At block 306 the extracted lipids are analyzed. For example, the lipids can be analyzed using a high performance liquid chromatography, gas chromatography, and/or mass spectrometer. In particular, the analysis at block 306 is looking to identify diabolic acids that are present in the sample.

At block 308 the extracted proteins are analyzed. For example, the proteins can be analyzed using a shotgun proteomics or protein probe methods. For example, the proteins can be analyzed using a TOF (time of flight) mass spectrometer coupled to a liquid chromatograph or a MALDI (matrix assisted laser desorption/ionization) unit. In some embodiments, the protein samples can be analyzed as mixed sample. In other embodiments, the protein samples can be treated with Thermotogale specific antibodies and visualized with fluorescence or other means of protein staining.

At block 310 the extracted nucleic acids are analyzed. For example, the extracted nucleic acids can be sequenced, can be identified by fragment size, or can be analyzed using specific DNA/RNA probes. In some embodiments, the nucleic acids can be amplified using specific DNA probes and then be compared to sequencing libraries such as Illumina MiSeq/HiSeq, or with versions of ABllon Torrent. In some embodiments, whole cells can be stained with RNA specific probes that are attached to a fluorophore, or detection of the fluorophore can be conducted using a confocoal or fluorescent microscope.

At block 312, the information from the extracted lipids, proteins, and/or nucleic acids can be used to detect ecology signatures specific to the Thermotogales order. This extracted information is then used at block 314 to assign taxonomy signatures to the sample identifying family, genus, and/or species of specific Thermotogales present in the sample. The family, genus, and species specific lipids and proteins can be identified by comparing the community lipids and proteins to known standards. Thermotogale specific DNA sequences can be identified using a bioinformatics pipeline to assign taxonomy to community samples (with exemplary pipelines being MOTHUR and QIIME) and using a standard sequence database (for example, SILVA, NCBI, GreenGenes) to determine which, if any, Thermotogale genera are represented in the sample. For specific DNA probes, the presence of an amplicon and then the specific sequence of the amplicon can be compared to known Thermotogale sequences to identify the specific genus and/or species of Thermotogale present. For the fluorescent probes, any fluorescence would indicate that a match was found by the probe, and thus, indicate the presence of the specific genus or species of Thermotogale being probed for.

The relative abundance of the Thermotogale present in the sample can then be used to predict the temperature of the hydrocarbon reservoir at block 316. The order Thermotogales consists of the family Thermotogaceae, which consists of the genera *Defluviitoga, Fervidobacterium, Geotoga, Kosmotoga, Marinitoga, Mesotoga, Oceanotoga, Petrotoga, Thermopalliu, Thermosipho*, and *Thermotoga*. The relative abundance of different genera can be used to indicate the temperature of the hydrocarbon reservoir. For example, communities in which *Petrotoga* and *Kosmotoga* are most abundant and favored occur at temperatures of less than 60° C., while communities in which *Thermotogoa* are most abundant and favored are at temperatures of 60 to 80° C., and communities where Archaea are favored and most abundant are at temperatures greater than 80° C. Thus, if 50-100% of the community comprises *Petrotoga, Kosmotoga*, or a mixture thereof, the hydrocarbon reservoir is indicated to have a temperature of less than 60° C., for example a temperature in the range of 40 to 60° C. If greater than 30% of the community comprises *Thermotoga*, less than 30% of the community comprises *Petrotoga*, and less than 30% of the community comprises *Kosmotoga*, the hydrocarbon reservoir is indicated to have a temperature of from 60 to 80° C. If the community comprises from 30 to 100% of Archaea, and less than 30% of *Thermotoga*, less than 30% of *Petrotoga*, and less than 30% *Kosmotoga*, then the hydrocarbon reservoir is indicated to have a temperature of greater than 80° C., such as from 80 to 100° C.

In some embodiments, the community structure of the samples from the hydrocarbon seep can be compared to the community structure of reference samples that are not from hydrocarbon seeps. Thus, it can be verified that the marker abundance in the samples from the seep is greater than the abundance in reference samples. If the markers are present and sufficiently abundant then the markers can be used to indicate that the sample did in fact come from a hydrocarbon seep and provide information about the conditions of the hydrocarbon reservoir. For example, a reference sample may be obtained at a location that is at least 200 meters, or at least 250 meters, or at least 300 meters, or at least 350 meters, or at least 400 meters, or at least 450 meters, or at least 500 meters away from the center of the location where the seep is emanating from the surface, and in some embodiments, less than 2000 meters, or less than 1750 meters, or less than 1500 meters, or less than 1250 meters, or less than 1000 meters away from the location where the seep is emanating from the surface.

Figure 3:
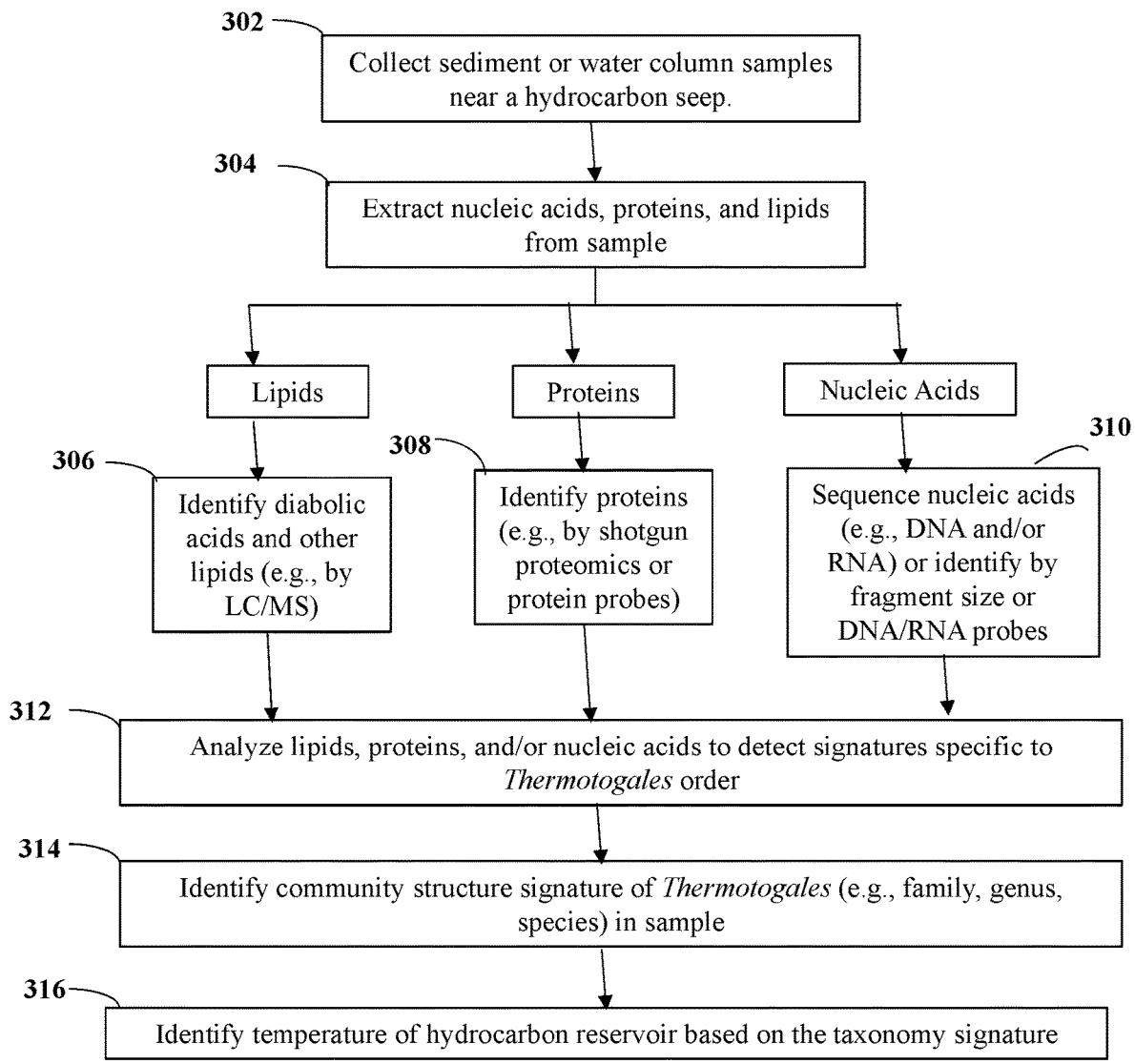
FIG. 3 is a block diagram of a workflow according to methodologies and techniques described herein.

The hydrocarbon reservoir properties that are identified using the taxonomic signature of the Thermotogales present in the sample that is identified with reference to FIG. 3, can be used in conjunction or refined with other information about the community function of the sample. For example, in the sediments and fluids surrounding a cold methane seep the following microorganisms might be found: *Desulfobacterium anilini, Desulfovibrio gabonensis, Archaeoglobus fulgidus Methanobacterium ivanovii*, ANME-1 (anaerobic methanotroph), and ANME-2. These are organism have common metabolic activities, and have a community function of reducing sulfate, oxidizing methane to $CO_2$, and reducing $CO_2$ back to methane. This information can then be used to infer other properties about the ecology of the hydrocarbon reservoir, such as salinity or pressure. Note that community structure does not necessarily imply knowledge about the community function. Likewise, geochemical or genetic information about a community function does not necessarily imply the presence or absence of specific species (i.e., community structure).

The determination of the community structure and the community function can thus be used, together with observing organism behavior interaction, measured physical and chemical conditions, and measured biological components and products, to derive and understand the ecology of the samples. The sample ecology may then be used to determine properties of the associated hydrocarbon reservoir. That is, as the sample ecology may vary depending on pressure, temperature, hydrocarbon type, and volume, the sample ecology may assist in determining pressures, temperatures, hydrocarbon type, and volumes associated with the sample and/or an associated reservoir.

In an aspect of the disclosed methodologies and techniques, a fluid sample is collected from a reservoir with known physical and chemical conditions. The ecology of this sample is described using the techniques defined herein. A sediment sample is collected from a hydrocarbon seep connected to the known reservoir. The ecology of this seep is described in the same manner. Key species are identified via their DNA, RNA and lipids that link the two samples together. Additionally key community functions are identified via proteins, transcripts and metabolites that relate the two environments to each other. These links can be used in exploration settings where the links between seeps and reservoirs are less definitive.

The indicators developed herein can be used to identify seeps that are likely linked to reservoirs. Seeps that are fed from shallow deposits or directly from the source rock will not have the same set of characteristics. Additionally, ecology in seafloor sediments can be used to identify smaller seeps that do not have physical surface expressions.

Paleo-seeps can be identified via intact lipids and metabolites in sediments. These compounds are stable enough to remain in the sediment for years after active seeping has ceased. Lipid derived compounds are commonly used to fingerprint oils in organic geochemistry. These compounds are stable over geologic time scales. Paleo-seeps may be associated with economic hydrocarbon reservoirs that are no longer receiving new charge from the source rocks.

In addition to conventional exploration, the methodologies described herein can also provide critical information during unconventional hydrocarbon exploration and development. Specifically, oil shale, shale gas and oil sand systems have properties that vary as a function of temperature, pressure, hydrocarbon type, inorganic mineralogy and chemistry. These properties can impact the predicted economic volumes that can be obtained from these unconventional reservoirs. Oil shale and shale gas are settings where the source rock is the reservoir, which means hydrocarbon migration is limited. Microbial products and biomarkers may help identify in situ pressures, temperatures and variations in hydrocarbon types across a geologic area of interest. Although this data would be obtained from test well samples, there is still an opportunity to calibrate basin and petroleum system models and constrain fluid or gas properties to better identify and extract resources. The role of indigenous microbial communities in controlling or altering the interface between mineral-hydrocarbon-aqueous phases may apply for the oil shale scenario, but are perhaps even more critical for oil sands. Typically, added microbial or fungal byproduct slurries are used to help alter subsurface conditions. This alteration is accomplished by the formation or addition of surfactants or by changing the hydrocarbon properties or composition. For example, converting viscous hydrocarbons to methane can help facilitate hydrocarbon extraction. The methodologies and techniques described herein may help optimize selection of zones, facies, or formations that have indigenous communities that may already produce or enhance hydrocarbon extraction without additional treatments. Specifically in oil sands, samples from multiple zones are combined to produce an aggregate that is then processed to remove the oil. If the proportions of these different materials are adjusted to include those that have increased natural surfactants, then this may increase the overall yield obtained from the homogenized aggregate.

If this data is tied to multiple other parameters that are indicative of pressure, temperature or salinity in the subsurface, then a more robust assessment may be made. Information about the reservoir, and the hydrocarbon system in general, may be missed by not incorporating or integrating other geological, geochemical and ecological information into traditional or currently existing workflows. This integrated approach is one option for which the methodologies described herein may be applied.

As a particular example, ascertaining that a particular hydrocarbon seep is connected to a subsurface hydrocarbon reservoir is an important piece of information that can be used to reduce the risks associated with exploring for oil and gas. That is, knowing that a hydrocarbon reservoir exists at a certain range of temperatures, pressures, and/or salinities narrows the region in which additional data must be collected before drilling a well. That is, the methodologies described herein allow one to focus exploration efforts on relevant depth intervals and/or depositional settings, and can ultimately affect ones decision on if, when, and where to drill an exploration well. For example, if it is found that a hydrocarbon seep is connected to a reservoir that has a temperature of less than 60° C., or from 60 and 80° C., or from 80° C. to 105° C., this temperature range can be converted to a reservoir depth using the geothermal gradient for the basin. Seismic survey can then be specifically designed and optimized for targeting that depth range, which can be reduce the overall cost of the survey.

Although the disclosed methodologies and techniques may be applied advantageously to oil and gas exploration activities, there are other ways in which said methodologies and techniques may be used, such as microbially enhanced oil recovery due to production of methane via methanogenesis, exopolysaccharides and enzymes causing changes fluid properties (e.g., viscosity), addition of microbial slurries to enzyme-activated proppants, and surfactants that change the interface between the hydrocarbons and minerals (e.g., emulsion breakers), reducing waxy components and increasing flow. In some cases the need to obtain microbial information is related to the potential for scale formation, reservoir souring, and pipeline corrosion if left untreated. Although reservoir fluid flow applications are based primarily on introducing biological tags downhole, critical information about how these biotechnology systems work may provide necessary insight into facies-specific properties and behavior, such as zones with unique indigenous ecology. From this type of data set, there is potential to target specific subsurface conditions or intervals and therefore optimize site selection based on a particular suite of desired properties. In all of these examples, a toolkit that appropriately identifies inherent and diagnostic information linked to ecologic and geochemical conditions in the subsurface will be helpful to de-risk some zones considered for exploring unconventional hydrocarbon plays or systems.

The disclosed methodologies and techniques provide a method that combines a full suite of geochemical and biological tools to identify organisms, their by-products, metabolites and the like that may be transported from the reservoir to the air-sediment or water-sediment interface with the fluids and hydrocarbons. This also includes differentiation of organisms living in association with the hydrocarbons, or related transported materials, at the interface that may shed light on hydrocarbon quality or changes therein due to transport and any degradation that may occur along the migration pathway. If extracellular DNA and other biomarkers are released within the reservoir, there is time for equilibration, reaction and association with reservoir geochemistry that may provide characteristic compositions that are retained during transport to surface and therefore provides more opportunity for assessing subsurface conditions. For example, the disclosed methodologies and techniques that combine metagenomic analysis, proteomics, lipid analysis, molecular geochemistry, biomarker and/or isotopic information will provide more information about the reservoir, ecology, and hydrocarbons and fluids therein than could be acquired from other approaches, such as PCR, quantitative PCR (qPCR), microarray or culturing methods alone.

The invention claimed is:

1. A method of determining one or more conditions of a hydrocarbon reservoir comprising:
   (a) obtaining a sample near a subsea hydrocarbon seep associated with the hydrocarbon reservoir, wherein the sample is obtained from a location that is within a radius of 150 meters from the center of the location where the seep is emanating from the seafloor;
   (b) extracting one or more of nucleic acids from the sample;
   (c) analyzing the extracted nucleic acids to identify signatures that are indicative of organisms from the Thermotogales order;
   (d) identifying the relative abundance of different genera or species of Thermotogales present in the sample and assigning a taxonomy signature to the sample;
   (e) using the taxonomy signature to determine the temperature of the hydrocarbon reservoir, wherein the hydrocarbon reservoir is identified as having a temperature of less than 60° C. when the taxonomy signature of the sample indicates that the sample contains 50-100% of microbes from the genera of *Petrotoga*, *Kosmotoga*, or a mixture thereof, wherein the hydrocarbon reservoir is identified as having a temperature of from 60° C. to 80° C. when the taxonomy signature of the sample indicates that the sample contains 40 to 100% of microbes from the genera of *Thermotoga*, less than 30% of microbes from the genera of *Petrotoga*, and less than 30% of microbes from the genera of *Kosmotoga*, and wherein the hydrocarbon reservoir is identified as having a temperature of greater than 80° C. when the taxonomy signature of the sample indicates that the sample contains less than 30% of microbes from the genera of *Thermotoga*, less than 30% of microbes from the genera of *Petrotoga*, less than 30% of microbes from the genera of *Kosmotoga*, and from 30-100% of the microbes that are Archaea.

2. The method of claim 1, wherein the sample is a fluid sample obtained from a water column near the hydrocarbon seep.

3. The method of claim 1, wherein the sample is a sediment sample obtained from the seafloor near the hydrocarbon seep.

4. The method of claim 1, wherein the sample is obtained from a location that is within a radius of 10 meters from the center of the location where the seep is emanating from the seafloor.

5. The method of claim 1, wherein the sample is obtained from a location that is within a radius of 3 meters from the center of the location where the seep is emanating from the seafloor.

6. The method of claim 1, further comprising preserving the obtained sample at a temperature at or less than −60° C. until the sample is ready to have the one or more nucleic acids extracted.

7. The method of claim 1, wherein the samples are analyzed to identify nucleic acid signatures that are indicative of organisms from the family Thermotogaceae.

8. The method of claim 1, wherein the samples are analyzed to identify nucleic acid signatures that are indicative of organisms from the genera *Defluviitoga, Fervidobacterium, Geotoga, Kosmotoga, Mariniloga, Mesotoga, Oceanotoga, Petrotoga, Thermopalliu, Thermosipho*, and *Thermotoga*.

9. The method of claim 1, wherein the samples are analyzed to identify nucleic acid signatures that are indicative of organisms from the genera *Petrotoga, Kosmotoga*, and *Thermotoga*.

10. The method of claim 1, wherein the taxonomy signature from the sample is calibrated by comparing the signature to a signature obtained from a reference sample that is obtained away from the hydrocarbon seep.

11. The method of claim 10, further comprising:
    obtaining a second sample from an area not associated with the hydrocarbon reservoir;
    extracting one or more of proteins, lipids, or nucleic acids from the second sample;
    analyzing the extracted proteins, lipids, or nucleic acids from the second sample to identify signatures that are indicative of organisms from the Thermotogales order;
    identifying the relative abundance of different genera or species of Thermotogales present in the second sample and assigning a taxonomy signature to the second sample;
    comparing the taxonomy signature of the second sample with the taxonomy signature of the sample taken from the hydrocarbon seep;
    using the compared taxonomy signature to determine the temperature of the hydrocarbon reservoir.

12. The method of claim 10, wherein the reference sample is obtained at a location that is at least 200 meters away from the center of the location where the seep is emanating from the surface.

13. The method of claim 1, wherein the nucleic acid analysis comprises one or more of DNA analysis, RNA analysis, and metagenomics.

14. The method of claim 1, further comprising using the determined temperature to determine the depth of the hydrocarbon reservoir.

15. The method of claim 14, wherein determining the depth of the hydrocarbon reservoir comprises using a geothermal gradient to determine the depth from the determined temperature.

16. The method of claim 14, further comprising conducting a seismic survey of the hydrocarbon reservoir, wherein the seismic survey is targeted at the determined depth.

17. The method of claim 14, further comprising using the determined depth to interpret seismic data of the hydrocarbon reservoir.

* * * * *